United States Patent [19]
Glenn et al.

[11] Patent Number: 5,221,483
[45] Date of Patent: * Jun. 22, 1993

[54] PROCESS AND APPARATUS FOR REMOVAL OF DNA, VIRUSES AND ENDOTOXINS

[75] Inventors: Stephan D. Glenn, Davie; Gregory Butchko, Miami Lakes; Edward O'Connell, Miami; Paulette Smariga, North Miami, all of Fla.

[73] Assignee: Coulter Corporation, Hialeah, Fla.

[*] Notice: The portion of the term of this patent subsequent to Nov. 26, 2008 has been disclaimed.

[21] Appl. No.: 787,061

[22] Filed: Nov. 4, 1991

Related U.S. Application Data

[63] Continuation-in-part of Ser. No. 546,011, Jun. 29, 1990, Pat. No. 5,076,933.

[51] Int. Cl.$^5$ .................... B01D 25/00; B01D 63/08; B01D 71/10
[52] U.S. Cl. .................... 210/641; 210/321.64; 210/335; 210/446; 210/500.29; 210/506; 210/651; 210/655; 422/1; 422/101; 435/311; 935/19
[58] Field of Search .......... 210/641, 651, 655, 321.64, 210/335, 446, 500.29, 506, 507, 508; 424/89; 422/1, 101; 935/19; 435/311

[56] References Cited

U.S. PATENT DOCUMENTS

| | | | |
|---|---|---|---|
| 4,168,300 | 9/1979 | Anderson et al. | 424/89 |
| 4,420,398 | 12/1983 | Castino | 210/641 |
| 4,431,545 | 2/1984 | Pall et al. | 210/641 |
| 4,473,474 | 9/1984 | Ostreicher et al. | 210/636 |
| 4,869,826 | 9/1989 | Wang et al. | 210/679 |
| 4,935,142 | 6/1990 | Sternberg | 210/634 |
| 5,076,933 | 12/1991 | Glenn et al. | 210/641 |

OTHER PUBLICATIONS

A. Issekutz, Journal of Immunological Methods, 61, pp. 275–280 (1983).
H. Borg et al., J. Physiol. Pharmacol., vol. 59, pp. 890–892 (1981).
Schleicher & Schuell Product Information Sheet No. 364.
G. Sofer, "Chromatographic Removal of P-rogens", Biotechnology, Dec., 1984, pp. 1035 et seq.
Gerba et al., "Applied & Environmental Microbiology"; 50: 1375–1377 (1985).
S. Minobe et al., J. Chromatography, 248: 401–408 (1982).

Primary Examiner—Robert A. Dawson
Assistant Examiner—Sun Uk Kim
Attorney, Agent, or Firm—Myron C. Cass

[57] ABSTRACT

A single filtration device containing coated filter membranes and absolute pore filters is provided in which the membranes and absolute pore filters are present in two sections of the filter device. The filter device will remove up to about 98% of the endotoxins in addition to removing viruses with an efficiency of at least $4.6 \times 10^5$ and DNA to less than 10 picograms per 500 mg sample.

24 Claims, 2 Drawing Sheets

PROCESS AND APPARATUS FOR REMOVAL OF DNA, VIRUSES AND ENDOTOXINS

RELATED APPLICATION

This application is a continuation-in-part of U.S. Ser. No. 07/546,011 filed Jun. 29, 1990, now U.S. Pat. No. 5,076,933, and entitled "PROCESS AND APPARATUS FOR REMOVAL OF DNA AND VIRUSES".

FIELD OF THE INVENTION

The present invention relates to a process for removing DNA and viruses from physiological fluids and medicant solution administered to humans and animals, and an apparatus for performing said process. More particularly, the invention is especially effective for removing DNA, viruses and endotoxins from biological pharmaceutical solutions and biological media, for example, DNA, viruses and endotoxins from a monoclonal antibody solution, buffer solutions or a solution of bovine serum albumin.

BACKGROUND OF THE INVENTION

One objective in the preparation of pharmaceutical solutions, buffer solutions, life support solutions, saline solutions and other such solutions which are to be administered to animals and humans is that they be as free as possible from substances which might cause an adverse reaction in the host. While a goal of zero contamination by substances such as DNA, viruses and endotoxins is always sought, in actual practice very minute amounts of such substances are sometimes present. The Food and Drug Administration (FDA) has set standards for such substances which cannot be exceeded. Manufacturers, ever mindful that a batch of medicant may be rejected if the level of such substances is too high, continually seek new methods to ensure that their products do not exceed FDA standards. Consequently, in all phases of the manufacturing process, manufacturers seek to ensure the purity of the reagents used in the manufacture as well as the final product. Many of the medicants and other products mentioned above are either sold as aqueous solutions or are manufactured in aqueous medium. Consequently, the manufacturers seek to ensure that the water they use is free of DNA, viruses and endotoxins.

One technology that such manufacturers often use is ultrafiltration. U.S. Pat. Nos. 4,431,545 to Pall et al, 4,816,162 to Rosskopf et al, and 4,420,398 to Castino, describe dual-module filtration to remove pathological and/or toxic substances from various fluids including water, blood and plasma. U.S. Pat. No. 4,431,545 utilizes dual filters, one of which has a negative zeta potential and one of which has a positive zeta potential, to filter out positively and negatively charged particles. Neutral particles are removed in accordance with the pore size ratings of the filters which are 0.01 microns or larger as disclosed. U.S. Pat. No. 4,816,162 describes an apparatus that removes immunoglobulins, albumin and lipoproteins from blood, blood plasma or serum, but does not describe the removal of DNA or viruses. The filter in this patent is designed for use in circulating and purifying blood during surgery. U.S. Pat. No. 4,420,398 describes a filtration method for separating cell produced antiviral substances, including monoclonal antibodies, from the reaction "broth" in which they are produced. This patent does not indicate whether the resulting species are free of viruses, endotoxins and DNA which may cause a reaction within a patient.

It is known in the prior art that multiple filtration with a 0.04 micron absolute pore size filter will remove viruses of 0.075 micron size, but not smaller viruses. For example, filtration of calf serum containing MS 2 phage (0.024 micron) through 0.04 micron will not remove the virus. In those circumstances where virus can be removed, removal rate is typically 99.9 to 99.99% per filter pass. For example, using a 0.04 micron filter, applicants removed all detectable Reovirus (0.075 micron) from a sample containing $10^8$ virus particles per milliliter sample. An article published in the April, 1990 issue of Genetic Engineering News (page 6) commented on the Food and Drug Administration's (FDA) increasing emphasis on viral removal protocols with regard to the preparation of biological pharmaceuticals and the efforts being made by filter manufacturers to achieve higher degrees of virus removal.

Another contaminant which can be present in biological pharmaceuticals such as monoclonal antibodies is DNA. It is generally felt in the industry that the FDA seeks to achieve a DNA level in monoclonal antibody preparations of less than 10 picograms of DNA per dose of monoclonal antibody.

Manufacturers of biological pharmaceutical such as monoclonal antibodies are required to establish Quality Assurance (QA) procedures to which verify that their products meet standards. In the procedures used to show compliance with the standards, it is necessary that the DNA in a sample be concentrated or solid phased (collected in solid form) from a solution of the biological pharmaceutical. It is known that DNA can be concentrated, solid phased or removed from solution by the use of diethylaminoethyl cellulose (DEAE) filter membranes. A manufacturer's literature (Schleicher & Schuell) indicates that DEAE filters will solid phase more than 90% of *E. coli* DNA from a solution containing 0.2 $\mu$g DNA/ml. In a more dilute solution containing 0.001 $\mu$g DNA (1 nanogram) more than 80% will be solid phased. The DEAE filters work by binding a protein such as DNA to the filter. However, a major limitation arises in the use of DEAE filters with some monoclonal antibody solutions. For example, it has been found that DNA measurements of monoclonal antibody containing buffer solution having components such as maltose can result in cause false high or low DNA values. In order to assure that the DNA assay values are accurate, these false readings must be eliminated.

Lastly, in addition to viruses and DNA, endotoxins are important contaminating substances in biological pharmaceuticals. While some manufacturers offer column packing materials which are useful in removing endotoxins from protein solutions such as solutions of monoclonal antibodies, such packing materials often result in low product yields after passage of the protein solution through the column. The DEAE filter membranes described above have also been reported to remove endotoxins. However, we have not found the membranes to be effective in removing endotoxins from all sources. In some instances removal is high, whereas in others it is low. This variation is believed to be due to structural variation of the endotoxins themselves in the various samples. The variations in the endotoxins are, in turn, believed dependent on the source of the endotoxin itself and on the chemical treatment it has been subjected to. Having done a careful study of the extant art, we have developed a single filtration device capable of removing virus, DNA and at least some endotoxins to lower levels than previously achieved.

SUMMARY OF THE INVENTION

A single filtration device or apparatus containing DEAE coated filter membranes and absolute pore filters is provided in which the membranes and absolute pore filters are present in two sections of the filter device. The first section of the device is the DNA filter section comprising a first 0.2 micron filter, a first DEAE filter, a second DEAE filter and a second 0.2 micron filter. The second section is the virus filter section comprising a first 0.1 micron filter, a second 0.1 micron filter, a first 0.04 micron filter, and a second 0.04 micron filter. The filter sections can be housed in a single filter device or, alternatively, the sections can be housed in separate housings provided that in use, the housing containing the DNA filter section precedes the housing containing the virus filter section and that the two are connected. In order to achieve higher levels of filtration than that afforded by a single device, multiple devices can be combined in series. The device may be used on a large scale at point of manufacturing or packaging a pharmaceutical solution, or it can be used on a small scale at the point of administration to a patient. In either case, the DNA and viruses are removed by passing the pharmaceutical solution through the DNA and virus filters by the use of either pressure to push the solution through the filter elements, as when administering to a patient, or vacuum to draw the solution through the filter elements as in some manufacturing procedures.

The apparatus embodying the invention will remove viruses, as modeled by type-C Xenotropic retrovirus, with an efficiency of at least $4.6 \times 10^5$ or approximately 99.995%, or $3 \times 10^{10}$ bacteriophage (99.99999997%) ; remove DNA from levels of 10 μg/sample to levels below 10 picograms per 500 mg sample of monoclonal antibody and preferably below 1 picogram per sample (100 ml of water or solution) and will remove at least 97% of some bacterial endotoxins. Further, these filter units absorb less than 10% of the pharmaceutical or biological pharmaceutical, and most often 6% or less of such pharmaceuticals particularly monoclonal antibodies and bovine serum albumin.

In an alternative embodiment of the invention, the DEAE filter membranes are replaced by absolute pore filters which have been coated with DEAE, QAE (quaternary aminoethyl salts), QAM (quaternary aminomethyl salts) and other like quaternary salts. For example, the first and second DEAE filter membranes can be replaced by 0.04 micron filters coated with QAE or QAM.

Another alternative embodiment of the invention is an improved apparatus wherein DEAE, QAE and QAM salts, and other like substances, are directly coated on or bonded to one or more of the 0.2, 0.1 and 0.04 micron absolute pore filters. The resulting absolute pore filters thereby replace the DEAE cellulose filters.

DETAILED DESCRIPTION OF THE INVENTION

Figure 1:
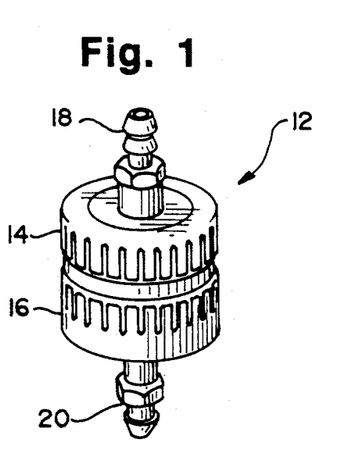
FIG. 1 is a perspective view of single unit of filter apparatus embodying the invention.

Referring to FIG. 1, the invention is a filter device 12 comprising a two-piece filter housing part having a top part 14 with inlet port 18, a base part 16 with outlet port 20 and a series of internal elements (not shown) with said top part and base part being joined together in a leakproof manner; for example, by screwing the two parts together, by ball and socket attachment or other such means.

Figure 2:
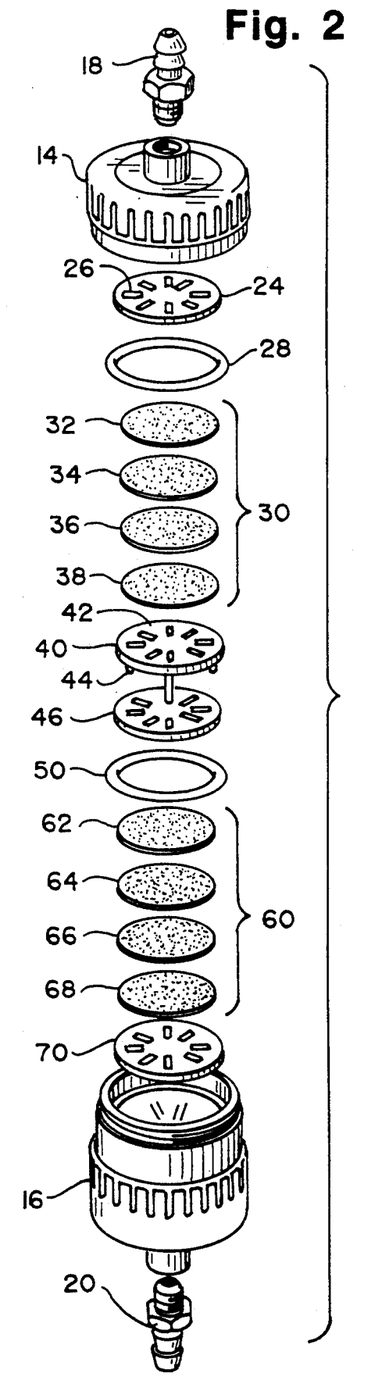
FIG. 2 is an exploded view of the apparatus shown in FIG. 1.

FIG. 2 is an exploded view of the device of the invention. The device comprises the visible external members 14, 16, 18 and 20 as described above and internal elements, said internal elements being a first flat filter support 24 having a plurality of channels 26 extending through the thickness of the support; a first sealing member 28 extending a lateral distance inward from the inner wall of the filter housing; a first filter section 30 having filter elements 32, 34, 36 and 38 in sequential facial contact from one to the other throughout; a filter support 40 with a flat top face 42 in contact with the bottom face of filter element 38, a plurality of channels 26 extending through the thickness of the support and a plurality of rigid legs 44 at the outer edge of the bottom face of said support; a second flat filter support 46 having a plurality of channels 26 extending through the thickness of the support and whose top face 48 is in contact with legs 44; a second sealing member 50; a second filter section 60 having filter elements 62, 64, 66 and 68 in sequential facial contact from one to the other throughout; a third flat filter support 70 having a plurality of channels 26 extending through the thickness of said support; and wherein the top to bottom face contact of the element is 28 to 24, 32 to 33, 34 to 32, 36 to 34, 38 to 36, 40 to 38, 50 to 46, 62 to 50, 64 to 62, 66 to 64, 68 to 66 and 70 to 68: and the top of face of element 24 is supported by the interior of top housing 14 and the bottom face of element 72 is supported by the interior of housing 16; and wherein sealing said interior elements by joining said top and base housing causes a pressure to be exerted on said sealing members 28 and 50 causing said sealing members to seal to the walls of said housing thereby preventing flow around filter sections 30 and 60, and forcing said flow to occur only through said filter sections.

Figure 3:
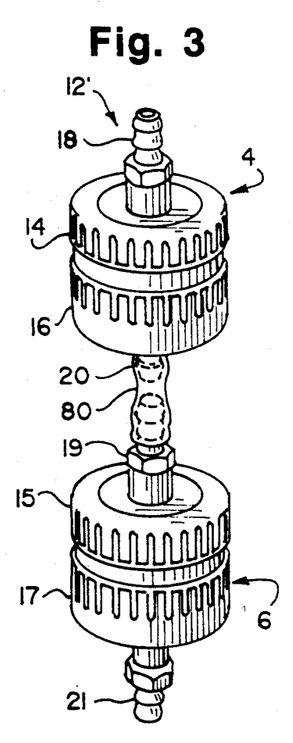
FIG. 3 is a perspective view of a multiple unit filter apparatus embodying the invention.

Referring to FIG. 3, a second embodiment of the invention is a two section filter device 12 having a first DNA removal filter unit 4 and a second virus removal unit 6 joined by a connecting means 80.

Figure 4:
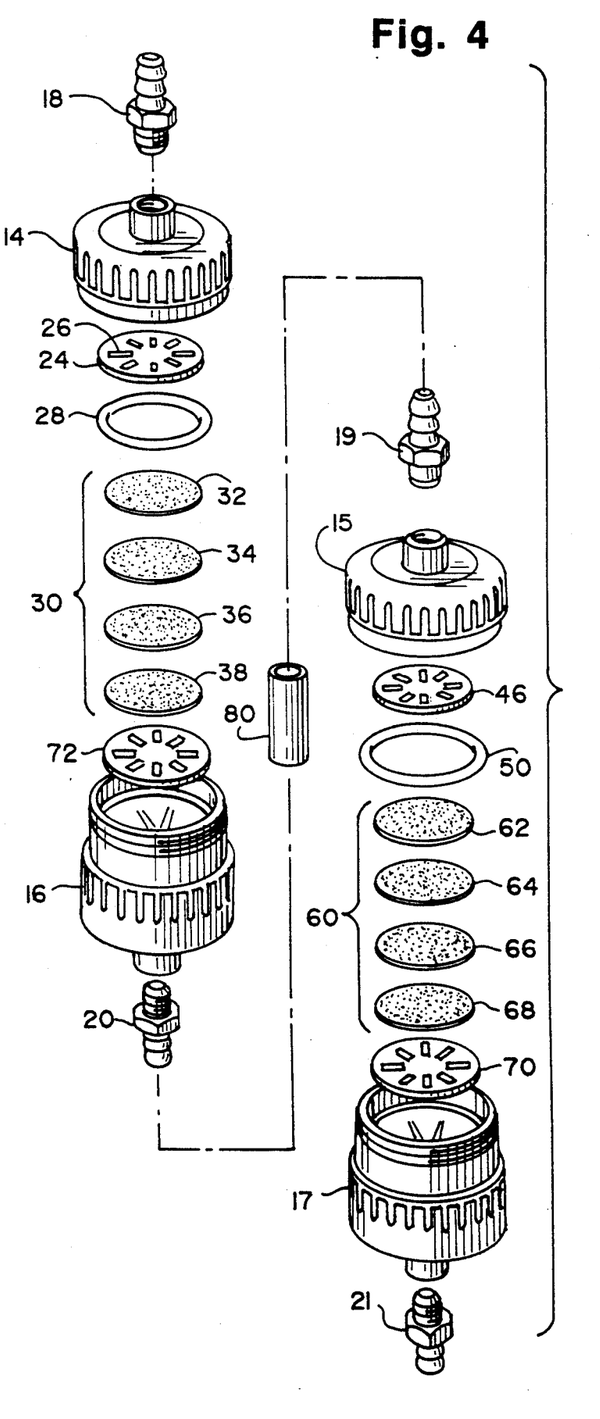
FIG. 4 is an exploded view of the apparatus shown in FIG. 3.

FIG. 4 is an exploded view of the two unit filter device as shown in FIG. 3 comprising a first DNA removal filter unit having a top filter housing part 14 with inlet port 18 and a base filter housing part 16 with outlet port 20, and internal members flush to the interior walls and sequentially in facial contact with each other; said internal members being a first flat filter support 24 having a plurality of channels 26 extending through the thickness of the support; a sealing member 28 in contact with the inner side walls of said housing and extending a lateral distance inward from the inner wall; a DNA filter section 30 having filter elements 32, 34, 36 and 38; a second flat filter support 72 having a plurality of channels extending through the thickness of the support; and a second virus removal filter unit 6 having a top filter housing part 15 with inlet port 19 and a base filter housing part 17 with outlet port 21 and internal members which are sequentially in facial contact with each other; said internal members being a first flat filter support 46 having a plurality of channels extending through of said support: a first sealing member 50 in contact with the inner side walls of said housing and extending a lateral distance inward from said inner wall; a virus filter section 60 having filter elements 62, 64, 66 and 68; and a filter support member 62 having a plurality of channels 26 extending through the thickness of said support; and a connecting member 80 joining said DNA filter unit 4 and said virus removal filter unit 6 by connecting outlet port 20 and inlet port 19; wherein the top to bottom face contact of the elements is 28 to 24, 32 to 28, 34 to 32, 36 to 34, 38 to 36, 72 to 38, 50 to 46, 62 to 50, 64 to 62, 66 to 64, 68 to 66, and 70 to 68; and top face of elements 72 and 70 is supported by the interior of their respective housings 14 and 15 and the bottom face of elements 72 and 70 is supported by the interior of their respective housings 16 and 17: and whereby enclosing said interior elements by joining respective top and base housings parts causes a pressure to be exerted on said sealing members thereby preventing flow around filter section 30 and 60, and forcing said flow to occur only through said respective filter sections; and said first DNA removal filter part and said second virus removal filter part being joined b connecting means 80 attached to parts 19 and 20.

The filter units as described above can be in any suitable size and shape possible, i.e., round, square or rectangular, subject only to limitation of the availability of size and shape of the filter material for filter sections 30 and 60. The filter units can be sized to handle commercially useful quantities of water for use in the manufacture or preparation of buffer solutions, pharmaceuticals, pharmaceuticals solutions and the like. The filter can be used at any point in a manufacturing processes where a new aqueous material is added and is especially useful in removing DNA, virus and endotoxins in the packaging step at the end of the manufacturing process. In addition, the filter system of the present invention can be used in conjunction with a device for administering a physiological or a pharmaceutical solution to a patient; for example, the filter system can be built into or placed into a hypodermic syringe. In all instances of use, the solution being filtered passes through the DNA removal filter section and then passes through the virus filter section.

The filter elements of the filter apparatus described above are a combination of diethylaminoethyl cellulose and absolute pore filters. These filters, when used in the apparatus of this invention, will remove a ca. 0.1 micron type-C retrovirus with an efficiency of $4.6 \times 10^5$ or higher, remove DNA to level of 10 micrograms/ml to levels below 1 picogram/ml and will remove about 97% of some bacterial endotoxins. Alternately viewed, the device removes DNA from a level of 10 micrograms/dose to levels below 1 picogram/dose. In addition, the filter elements of the present invention absorb 6% or less of proteins from the solution under treatment: for example, monoclonal antibody or bovine serum albumin solution. In the preferred embodiment of the invention elements 32 and 38 are 0.2 micron absolute pore filters; elements 34 and 36 are DEAE coated filters such as, for example, Schleicher & Schuell's NA45 filters; elements 62 and 64 are 0.1 micron absolute filters; and elements 66 and 68 are 0.04 micron absolute pore filters. In the preferred embodiment of the invention, infectious virus particles of about 0.108 micron size can be removed with an efficiency of at least 99.99% per passage through the filtration apparatus. Higher efficiencies can be obtained by using two or more of the filter apparati in series.

In a process utilizing the apparatus of this invention, the water, aqueous buffer solutions and pharmaceutical solutions, including biological pharmaceutical solutions, have a pH in the range of 3 to 9. Further, these solutions have a specific salt content of less than 0.5 Molar, said specific salts being one or more selected from the group consisting of the lithium, sodium, potassium or ammonium salts of the phosphate, chloride, bromide, iodide, sulfate and acetate anions. When utilizing the device of this invention, solutions are first passed through the DNA removal section prior to passage through the virus removal section.

The following examples are given to illustrate the utility of the present invention and are not to be construed as limiting the scope of the invention.

EXAMPLE 1

Virus Removal

The internal elements of the filter unit of the invention were assembled using eight filter element in the sequence 0.2 micron, DEAE, DEAE, 0.2 micron, 0.1 micron, 0.1 micron, 0.04 micron and 0.04 micron. The 0.2, 0.1 and 0.04 micron elements were absolute pore filters, and the DEAE elements were NA 45 filter (Schleicher & Schuell). The units were sealed in autoclavable syringes and were autoclaved or gas sterilized using standard procedures. The sterilized syringes containing the filter elements were sent to Microbiological Associates, Inc., Life Sciences Center, 9900 Blackwell Road, Rockville, Md. 20850 for evaluation with monoclonal antibody solutions spiked with mouse xenotropic retrovirus of similar size to type C retrovirus (0.1 micron v 0.104 micron respectively). Each syringe filter device was evaluated against one sample of retrovirus spiked monoclonal antibody. By S+L− assay, the samples contained $4.37 \times 10^5$, $5.6 \times 10^5$ and $4.1 \times 10^5$ FFU/ml.

$$FFU/ml = \text{(mean number of foci/dish} \times \frac{1}{\text{volume/dish}} \times \frac{1}{\text{dilution}}]$$

After passage of the test samples through the syringe filter units, the filtrates were re-analyzed in triplicate for retrovirus. No retrovirus found in any of the three monoclonal antibody filtrates. Antibody recovery was greater than 90%.

EXAMPLE 2

Removal Of Bacteriophage By DNA/ Virus Removal Filters.

The maximum concentration of xenotropic retrovirus attainable is about $10^6$ FFU/ml. In order to validate the DNA/Virus removal filters of this invention for higher virus particle removal efficiencies, bacteriophage T4 (approximately 0.1 micron) was chosen as a second model virus. The assay for bacteriophage T4 concentration was the formation of plaques (PFU) on a lawn of

*Escherichia coli* B (ATCC 11303). The bacteriophage T4 was grown to maximum concentration ($9.9 \times 10^{10}$ PFU/ml) and the undiluted bacteriophage solution was divided into three aliquots. Each aliquot was filtered through a separate DNA/Virus removal filter device. The concentration of bacteriophage T4 in the filtrate was assayed by dilution and plating on dishes of *E. coli*. None of the three filtrates contained viable virus. The assay has an uncertainty of 3.3 FFU. These results indicate that the DNA/Virus removal filter device of the present invention is capable of reducing the concentration of an 0.1 micron bacteriophage by at least $3.0 \times 10^{10}$ fold (99.99999997%). Similar results should be obtainable with viruses of similar size, approximately 0.1 micron, such as type C retrovirus. Type C retrovirus has been found to be a contaminant in the conditioned raw material for monoclonal antibody pharmaceutical. To the inventors' knowledge, no single pass through any filter device as previously achieved this level of virus removal. Use of the filter device of the present invention should reduce the concentration of type C retrovirus in the conditioned raw material by at least $3 \times 10^{10}$ fold. Thus, solutions containing nominal virus counts on the order of $10^7$ should be able to be filtered to an undetectable virus level with a 1000 fold safety margin. In those cases where the virus load of a solution is higher, over $10^7$, the solution can be filtered two or more times to obtain a solution having an undetectable virus level. Using two of the filter devices of the present invention in series would allow the removal of approximately $10^{17}$–$10^{18}$ virus particles per ml $[(3 \times 10^{10}) \times (3 \times 10^{10})/1000 = 9 \times 10^{17}]$.

EXAMPLE 3

DNA Removal From Spiked Antibody solutions

Monoclonal antibody solutions containing 400 mg of antibody each and DNA were filtered through the DNA/virus removal filter unit of the invention. DNA analysis before and after filtration showed 727 pg and 442 pg of DNA per sample before filtration; and 5 pg and 1 pg DNA, respectively, after filtration (99.3% and 99.8% removal).

EXAMPLE 4

DNA Removal From Commercial Antibody Solutions

Analysis of commercial monoclonal antibody solutions indicated that there is significant DNA contamination. The analysis was performed using an assay kit from FMC Bio Product's, Rockland, Me. (FMC assay) for the detection of DNA solid-phased on Nylon 66 membranes. Five lots of DNA containing monoclonal antibody solution were analyzed for DNA before and after filtration through a filter apparatus of the invention: All filtered solutions had less than 10 picograms of DNA per dose of antibody and two of the five showed less than 1 picogram per dose. The results are shown in Table 1.

TABLE 1

SUMMARY of DNA REMOVAL from antibody products

| Product No. | Mean DNA Before Filtration | | Concentration After Filtration |
|---|---|---|---|
| | pg DNA/mg Mab | pg DNA/dose | pg DNA/dose |
| 1 | 0.65 | 260 | 2.6 |
| 2 | 0.30 | 120 | 0.4 |
| 3 | 0.34 | 3.4 | 2.6 |
| 4 | 0.13 | 1.3 | 3.1 |
| 5 | 0.13 | 140 | 0 |

EXAMPLE 5

DNA Removal Validation

In order to validate DNA removal for commercial purposes, the DNA/virus removal filters were challenged with 500 mg samples of a pharmaceutical grade monoclonal antibody (B1) in buffer spiked with 100 micrograms of hybridoma produced DNA. The DNA used in the validation was purified from the same cell culture medium used to produce monoclonal antibodies and was as similar as possible to the DNA actually encounted in the production of the antibody. Three antibody solutions were spiked with the DNA. Two unspiked antibody solutions, two buffer (only) solutions without DNA and two buffer (only) solutions spiked with 100 micrograms of DNA were used as controls. The actual level in the spiked solutions was determined by means of a fluorescent DNA assay technique. The spiked antibody solutions were found to have actual DNA levels of 81, 92 and 74 micrograms per sample. The spiked buffer solutions were found to have actual DNA levels of 89 and 96 micrograms per sample. All solutions samples were equal volume.

Each of the test solutions (9 solutions total) was filtered through a separate 25 mm DNA/Virus removal filter apparatus. The residual DNA in each filtrate was concentrated, solid phased and quantified in duplicate using standard FMC DNA assay techniques. The quantity of DNA in each assay was determined from a standard curve of purified hybridoma DNA run in the same assay. For the standard curve, the color intensities of the sample bands, measured by the instrument's reflection densitometer, are measured as peak heights in centimeters. The standard curve data is linearly transformed by a log-logit transformation where the peak heights are converted to a logit (relative to a standard that will give maximum color development and a blank) versus the log of the picograms of DNA standard added. Test samples were then interpolated from the standard curve of DNA to color intensity. The results are given in Table 2 and indicate that a single pass through the DNA/Virus removal filter is capable of reducing the DNA levels by about $10^7$ fold to approximately 10 picograms DNA per dose of antibody (mean = 12.3 pg DNA/500 mg antibody). The mean value for an equal volume of unspiked buffer (only) is 6.2 pg. Therefore, the mean net DNA detected in the filtered, spiked antibody solution is 6.1 pg DNA/500 mg antibody.

TABLE 2

| Sample | DNA Spike | DNA Detected in sample after DNA spiking | % Recovery of protein concentration (Lowry) | Mean total DNA detected after filtration | Mean |
|---|---|---|---|---|---|
| B1 500 mg | 100 ug | 81 ug | 98.9% | 16.5 pg | |
| B1 500 mg | 100 ug | 92 ug | 89.0% | 8.6 pg | 12.3 pg |

TABLE 2-continued

| Sample | DNA Spike | DNA Detected in sample after DNA spiking | % Recovery of protein concentration (Lowry) | Mean total DNA detected after filtration | Mean |
| --- | --- | --- | --- | --- | --- |
| B1 500 mg | 100 ug | 74 ug | 96.7% | 11.7 pg | |
| B1 500 mg | 0 | 0 | 96.3% | 3.3 pg | |
| B1 500 mg | 0 | 0 | 92.8% | 3.2 pg | 3.2 pg |
| Buffer | 100 ug | 89 ug | N/A | 16.9 pg | |
| Buffer | 100 ug | 96 ug | N/A | 3.3 pg | 10.1 pg |
| Buffer | 0 | 0 | N/A | 9.8 pg | |
| Buffer | 0 | 0 | N/A | 2.6 pg | 6.2 pg |

*total DNA in 500 mg sample of monoclonal antibody (mean observation of samples assayed in duplicate.)

EXAMPLE 6

Endotoxin Removal

A 100 ml solution of 50 mg/ml bovine serum albumin in 10% maltose-phosphate buffer solution contaminated with DNA and an endotoxin was filtered through a 47 mm DNA/Virus removal filtration device. The starting solution contained 248 pg/ml DNA and 1966 endotoxin units/ml (EU/ml)/

First, middle and end 20 ml portions of filtrate were collected and analyzed. No DNA was detected in any analyzed portion of filtrate. Endotoxin levels were: first=30.72 EU/ml, middle=30.72 EU/ml and last=61.44 EU/ml. Endotoxin removal in the end sample was 96.9%. Solution recovery was 95% (95 ml) with no change in protein concentration.

CONTINUATION-IN-PART DISCLOSURE

BACKGROUND OF THE INVENTION

Endotoxins are undesirable contaminants in parenteral drugs which can cause fever or a toxic reaction in the drug host. The upper limit for endotoxins in parenteral drugs generally acceptable to the U.S. Food and Drug Administration (FDA) is 5 EU/kg body weight/hour infusion. A manufacturer's release criteria for parenteral drugs such as monoclonal antibodies generally includes a specification for the maximum allowable endotoxin concentration. Production lots of parenteral drugs that fail to meet the specification release criteria must either be further processed to reduce the endotoxin concentration or be scrapped.

Column chromatography procedures for the removal of endotoxins have been described by H. Borg et al., Can. J. Physiol Pharmacol., 59: 890-892 (1081); A. C. Issekutz, J. Immunological Methods, 61: 275-281 (1983); and in Biotechnology December, 1984, pp 1035-1038. Column chromatography, however, entails considerable expense in equipment, chromatographic materials and waste disposal. Often it also results in a reduction in net product yield, thus increasing product cost. The invention described herein uses filter membranes, absolute pore filters and/or coated absolute pore filters to reduce the endotoxin level in aqueous buffer solutions, aqueous pharmaceutical solutions and aqueous biological pharmaceutical solutions.

SUMMARY OF THE INVENTION

A single filtration device or apparatus containing DEAE coated filter membranes and absolute pore filters is provided which can remove up to 98% of the endotoxins present in aqueous buffer solutions, aqueous pharmaceutical solutions and aqueous biological pharmaceutical solutions. The filter membranes and absolute pore filters provided by the invention are present in two sections of the device. The two sections of the device may be present in a single housing or may be in separate housings. The first section of the device is the DNA/endotoxin removal section and the second section is the virus/endotoxin removal section. In an alternate embodiment of the device, the filter membranes are removed and replaced by at least one absolute pore filter coated with DEAE, QAM or QAE salts and the like substances, or mixture thereof. In yet another embodiment, the filter membranes are removed and at least one of the remaining absolute pore filters is coated with DEAE, QAM or QAE salts and the like substances, or mixture thereof.

DETAILED DESCRIPTION OF THE INVENTION

The invention describes a process for the removal of DNA, endotoxins and viruses from aqueous buffer solutions, aqueous pharmaceutical solutions and aqueous biological pharmaceutical solutions by passing such solutions through a first DNA/endotoxin filter section and a second virus/endotoxin filter section, wherein the DNA, viruses and endotoxins are substantially removed, and collecting the aqueous buffer solutions, aqueous pharmaceutical solutions or aqueous biological pharmaceutical solutions. The filter device comprises a first DNA/endotoxin filter section having:

(I) (A) (i) a first absolute pore filter;
 (ii) a first and second filter selected from one of the group of (a) a DEAE cellulose filter membrane and (b) an absolute pore filter coated with at least one of the group consisting of diethylaminoethyl (DEAE) salts, quaternary aminoethyl salts and quaternary aminomethyl salts and the like; and
 (iii) a second absolute pore filter; or
(B) plurality of absolute pore filters at least one of which is coated with at least one selected from the group consisting of diethylaminoethyl (DEAE) salts, quaternary aminoethyl salts, quaternary aminomethyl salts and the like; and
(II) a second virus filter section comprising absolute pore filters of a smaller diameter than the absolute pore filters or coated absolute pore filters in the DNA filter section Samples from several lots of monoclonal antibody preparations were filtered through the filter device. The endotoxin concentration (endotoxin units ,EU) of the sample solutions was measured by the Limulus Amebocyte Lysate (LAL) assay. The Associates of Cape Cod LAL (Cape Cod, Mass.) assay was used which has a maximum sensitivity of 0.06 EU/ml. The endotoxin standard has a stated activity of 10 EU/ng. Endotoxin endogenous to the purified monoclonal antibody products was used without spiking with purified endotoxin material. The LAL assay for bacterial endotoxins is described in the United States Pharmacopeia, USP XXII <85>.

TABLE 3

Reduction in concentration of LAL quantified endotoxin by filtration of monoclonal antibody products through the DNA/Endotoxin/Virus filter device.*

| Lot or Exp. No. | Volume Filtered ml | Filter Size mm2 | Concentrations | | |
|---|---|---|---|---|---|
| | | | mAb mg/ml | Endotoxin EU/mg. | |
| | | | | Before Filtration | After Filtration |
| 1787-84A | 10 | 25 | 5 | 0.10 | ≦0.01 |
| 1825-1A | 50 | 25 | 20 | 0.77 | 0.01 |
| 1825-1B | 50 | 25 | 20 | 0.77 | ≦0.01 |
| 1825-1C | 50 | 25 | 20 | 0.77 | 0.77 |
| 5309001 | 30 | 25 | 7.12 | 8.63 | 0.33 |
| 5061002 | 568 | 90 | 5.01 | 24.35 | 0.77 |
| 5190002 | 91 | 90 | 20.74 | 0.09 | 0.01 |
| 5011001 | 80 | 90 | 53.08 | 0.02 | 0.01 |
| 5321007 | 60 | 90 | 42.90 | 0.04 | 0.01 |
| 5351001 | 63 | 90 | 21.64 | 0.02 | 0.01 |

*Monoclonal antibody products were tested by LAL assay for endotoxin concentration before and after treatment with the DNA/Endotoxin/Virus removal filter device.

The results in Table 3 illustrate that the endogenous endotoxin concentrations in the pharmaceutical grade monoclonal antibody preparations can be reduced by the DNA/Endotoxin/Virus removal filter device embodying the invention. The filter device reduced the endotoxin concentration in these products by up to 98%. The observed reduction in endotoxin level of these monoclonal antibody products is sufficient to allow administration of these products at higher doses and/or greater infusion rates with reduced risk to the patient receiving the drug.

EXAMPLE 7

Endotoxin Removal After Passage Through The Filter Device

The data presented in Table 1 indicates that lots of antibody product which could not be used can be salvaged by filtering through the DNA/Endotoxin/Virus filter device of the invention. For example, Lot 5061002 is a pharmaceutical grade monoclonal antibody which was not acceptable for its intended parenteral use because its endotoxin concentration of 24.35 E.U./mg was too high to allow infusion of the desired dosage in a reasonable time (product specification is 5 E.U./mg). The standard cost value of this product was $50,000 which would have been lost if the product had been scrapped. However, after filtration through the DNA/Endotoxin/Virus filter device, the endotoxin concentration was reduced to an acceptable 0.77 E.U./mg.

EXAMPLE 8

Evaluation of Endotoxin Removal After Passage Through the First and Second Sections of the Filter Device.

The data presented in Table 3 and Example 7 indicated the total amount of endotoxin removed after passage through the filter device of the invention. In this example, the amount of endotoxin removed by each filter section was measured. The results indicate that both sections are effective in removing endotoxins from the sample.

A 30 SDG mL sample of a 7.12 mg/mL solution of monoclonal antibody Lot Number 5309001 was passed through a 47 mm diameter filter device. The DNA/endotoxin removal section contained two 0.2 micron filter membranes and two NA45 filter (Schleicher & Schuell). The virus/endotoxin section contained two 0.1 and two 0.04 micron filters assembled as described above. Endotoxin levels in the sample were measured before filtering, after passage through the DNA/endotoxin section but not the virus/endotoxin section, and after passage through both the DNA/endotoxin section and the virus/endotoxin section. Test results were:

| Sample Test | Endotoxin Level |
|---|---|
| Before Filtration | 8.6 EU/mg antibody |
| Between Sections | 0.6 EU/mg antibody |
| After Both Sections | 0.3 EU/mg antibody |

The analyses show that 93% of the endotoxins were removed by passage through the DNA/endotoxin section and 96.5% (an additional 3.5% of endotoxin, 50% of residual endotoxin) were removed by passage through both filter sections.

EXAMPLE 9

Removal of Virus Particles

The results obtained in Example 2 showed that this DNA/Endotoxin/Virus removal filter device can reduce the concentration of the bacteriophage T4 in a sample by at least a factor of $3 \times 10^{10}$. This example represents an additional experiment to determine whether the virus in the original experiment was inactivated or fragmented, and whether the inactivated virus or subunits thereof passed through the filter device.

The bacteriophage T4 was grown to a concentration of $5 \times 10^{10}$ plaque forming units/ml. The bacteriophage suspension was then filtered through a DNA/Endotoxin/Virus removal filter device, the filtrate pelleted by ultracentrifugation and examined by transmission electron microscopy for T4 bacteriophage and T4 bacteriophage subunits. Neither T4 bacteriophage not T4 subunits were observed. Based on the number of negative grids observed, the concentration of particles in the filtrate was less than $1.73 \times 10^5$/ml. This result indicates that at least 99.9997% of the virus particle subunits were removed from the test solution suspension.

We claim:

1. A process for the removal of DNA, viruses and about 98% of endotoxins from aqueous buffer solutions, aqueous pharmaceutical solution and aqueous biological pharmaceutical solutions comprising, passing one of said aqueous buffer solutions, aqueous pharmaceutical solutions and aqueous biological pharmaceutical solutions through a first DNA/endotoxin filter section and a second virus/endotoxin filter section, wherein said DNA, viruses and endotoxins are substantially removed; and collecting said aqueous buffer solutions, aqueous pharmaceutical solutions or aqueous biological pharmaceutical solutions;

(I) said first DNA/endotoxin filter section having:
(A) (i) a first absolute pore filter,
(ii) a first and second filter selected from one of the group consisting (a) a DEAE cellulose filter membrane, and (b) an absolute pore filter coated with at least one of the group consisting of diethylaminoethyl salts, quaternary aminoethyl salts and quaternary aminomethyl salts, and
(iii) a second absolute pore filter; or (B) plurality of absolute pore filters at least one of which is coated with at least one selected from the group consisting of dimethylaminoethyl salts, quaternary aminoethyl salts, and quaternary aminomethyl salts; and
(ii) said second virus/endotoxin filter section having absolute pore filters of a smaller diameter than the absolute pore filters or coated absolute pore filters in the DNA/endotoxin filter section 2. The process in accordance with claim 1 wherein the yield of pharmaceuticals, including biological pharmaceuticals, in the filtered solutions is 90% or higher compared to the starting solution.

3. The process in accordance with claim 1 wherein the virus removal is 99.9999997% or higher when the virus is 0.100 microns or larger, and the yield of pharmaceutical or biological pharmaceutical in the filtered solution of same is 90% or higher compared to the starting solution.

4. The process in accordance with claim 1 wherein said DNA in the filtered solutions is preferably less than 10 picograms per 100 ml of solution.

5. The process in accordance with claim 4 wherein said DNA in the filtered solutions is less than 1 picogram per 100 ml of solution.

6. The process in accordance with claim 1 wherein the aqueous buffer solutions, aqueous pharmaceutical solutions and aqueous biological pharmaceutical solutions have a pH in the range of 3 to 9.

7. The process in accordance with claim 1 wherein the aqueous buffer solutions, aqueous pharmaceutical solutions and aqueous biological pharmaceutical solutions each have a specific salt content of less than 0.5 Molar, said specific salt being one or more selected from the group consisting of the lithium, sodium, potassium and ammonium salts of the phosphate, chloride, bromide, iodide, sulfate, and acetate anions.

8. A process for the removal of DNA, viruses and about 98% of endotoxins from aqueous pharmaceutical solutions "and aqueous biological pharmaceutical solutions", said process comprising passing either one of the solutions through a first DNA/endotoxin filter section and a second virus/endotoxin filter section to obtain a filtered aqueous pharmaceutical solution or a filtered aqueous biological pharmaceutical solution having substantially reduced DNA, virus and endotoxin levels, said solutions passing through:
(a) a first 0.2 micro absolute pore filter, a first diethylaminoethyl cellulose filter, a second diethylaminoethyl cellulose filter and a second 0.2 micron absolute pore filter in the first DNA/endotoxin filter section, and
(b) a first 0.1 micron absolute pore filter, a second 0.1 micron absolute pore filter, a first 0.04 micron absolute pore filter and a second 0.04 micron absolute pore filter in the virus/endotoxin filter section; and collecting the filtered solutions.

9. A process in accordance with claim 8 wherein the yield of the pharmaceutical, including biological pharmaceutical, in the filtered solution is 90% or higher.

10. A process in accordance with claim 8 wherein the virus removal is 99.9999997% or higher when the virus is 0.100 microns or larger, and the yield of the pharmaceutical or biological pharmaceutical in the filtered solution is 90% or higher.

11. A process in accordance with claim 8 wherein the DNA in the filtered pharmaceutical or biological pharmaceutical solution is reduced to less than 10 picograms per 100 ml of solution.

12. The process in accordance with claim 11 wherein the DNA in the filtered pharmaceutical of biological pharmaceutical solution is reduced to less than 1 picogram per 100 ml of solution.

13. A process in accordance with claim 8 wherein the pharmaceutical solution or biological pharmaceutical solution has a pH in the range of 6 to 8.

14. A process in accordance with claim 8 wherein the pharmaceutical or biological pharmaceutical has a specific salt content, excluding salts of pharmaceuticals or biological pharmaceuticals, of less than 0.5 Molar, said specific salts being at least one selected from the group consisting of the lithium, sodium potassium and ammonium salts of the phosphate, chloride, bromide, iodide, sulfate and acetate anions.

15. A process in accordance with claim 1 or 8 wherein said aqueous buffer solutions, aqueous pharmaceutical solutions and aqueous biological pharmaceutical solutions are passed through said DNA/endotoxin filter and said virus/endotoxin filter by a vacuum means or a pressure means.

16. An improved device for the removal of DNA, viruses and about 98% of endotoxins from aqueous buffer solutions, aqueous pharmaceutical solution and aqueous biological pharmaceutical solutions, said device having a housing with suitable inlet/outlet means, internal gaskets and filter supports, and internal filters, wherein the improvement comprises:
(a) a first DNA/endotoxin filter section having, from inflow to outflow, a first 0.2 micron filter and a second 0.2 micron filter, the filters having face-to-face contact;
(b) a second virus/endotoxin filter section having, from inflow to outflow, a first 0.1 micron filter, a second 0.1 micron filter, a first 0.04 micron filter and a second 0.04 micron filter, said filters having face-to-face contact; and
(c) DEAE functional groups, QAE functional groups, QAM functional groups or other quaternary amine functional groups bonded directly to one or more of the 0.2, 0.1 and 0.04 micron absolute pore filters.

17. An improved device in accordance with claim 16 wherein said 0.2, 0.1 and 0.04 filters are absolute pore filters.

18. The improved device of claim 16 wherein said device is capable of removing 99.9999997% of virus when the virus is 0.100 microns or larger.

19. The improved device of claim 16 wherein the device gives a yield of pharmaceutical or biological pharmaceutical in the filtered solution of 90% or higher compared to the unfiltered solution.

20. The improved device of claim 16 where the solution to be filtered is passed through said device by pressure or vacuum means.

21. The improved device of claim 16 wherein said device is a means of administration of said aqueous buffer solution, aqueous pharmaceutical solution or said aqueous biological pharmaceutical solution to a patient which means contains said DNA/endotoxin and virus/endotoxin filter sections.

22. The improved device of claim 16 wherein said device is a syringe filtration apparatus containing sad DNA/endotoxin and virus/endotoxin removal filters.

23. The improved device in accordance with claim 16 wherein aid device is preferably capable of removing DNA to a level of less than 10 picograms per 100 ml solution.

24. The improved device in accordance with claim 23 wherein said device is capable of removing DNA to a level of less than 1 picogram per 100 ml of solution.

* * * * *

UNITED STATES PATENT AND TRADEMARK OFFICE
CERTIFICATE OF CORRECTION

PATENT NO. : 5,221,483

DATED : June 22, 1993

INVENTOR(S) : Stephan D. Glenn, Gregory Butchko, Edward O'Connell and Paulette Smariga It is certified that error appears in the above-indentified patent and that said Letters Patent is hereby corrected as shown below:

Column 3, line 45, after "pharmaceuticals" insert --,--;

Column 4, line 37, change "32 to 33" to --32 to 28--;

Column 5, line 4, after "through" insert --the thickness--;

lines 16-17, change "elements 72 and 70" to --elements 24 and 46--;

line 27, change "joined b" to --joined by--;

Column 6, line 30, change "NA 45 filter" to --NA 45 filters--;

UNITED STATES PATENT AND TRADEMARK OFFICE
CERTIFICATE OF CORRECTION

PATENT NO. : 5,221,483
DATED : June 22, 1993
INVENTOR(S) : Stephan D. Glenn, Gregory Butchko, Edward O'Connell and Paulette Smariga It is certified that error appears in the above-indentified patent and that said Letters Patent is hereby corrected as shown below:

Column 8, line 67, change "89.0%" to --98.0%--;

Column 9, line 50, after "Biotechnology" insert --,--;

Column 12, line 44, change "virus particle subunits" to --virus particles or subunits--;

line 49, change "solution and" to --solutions and--;

Column 13, line 46, change "micro" to --micron--;

Column 14, line 62, change "aid" to --said--.

Signed and Sealed this

Twenty-seventh Day of September, 1994

Attest:

BRUCE LEHMAN

*Attesting Officer*   *Commissioner of Patents and Trademarks*